United States Patent [19]

Nagata et al.

[11] Patent Number: 5,304,577
[45] Date of Patent: Apr. 19, 1994

[54] MEDICAL OR DENTAL HARDENING COMPOSITIONS

[75] Inventors: Norifumi Nagata; Takayuki Yogoro, both of Sakura; Sadayuki Yuhda; Masahiko Ueda, both of Kawanishi, all of Japan

[73] Assignees: Onoda Cement Co., Ltd.; Sankin Kogyo Kabushiki Kaisha, Japan

[21] Appl. No.: 877,895

[22] Filed: May 1, 1992

[30] Foreign Application Priority Data

May 1, 1991 [JP] Japan ................. 3-100216
Jul. 19, 1991 [JP] Japan ................. 3-179916

[51] Int. Cl.$^5$ .............. C08K 3/32; C03C 10/02
[52] U.S. Cl. ....................... 524/417; 524/415; 523/113; 523/115; 523/116; 501/10
[58] Field of Search ........... 523/113, 115, 116; 524/415, 417; 501/10

[56] References Cited

U.S. PATENT DOCUMENTS

| | | | |
|---|---|---|---|
| 3,981,736 | 9/1976 | Broemer et al. | 501/10 |
| 4,366,253 | 12/1982 | Yagi | 501/10 |
| 4,636,526 | 1/1987 | Dorman et al. | 524/417 |
| 4,652,534 | 3/1987 | Kasuga | 501/10 |
| 4,677,140 | 6/1987 | Shiotsu | 524/417 |
| 4,698,318 | 10/1987 | Vogel et al. | 501/10 |
| 4,820,660 | 4/1989 | Mohri et al. | 501/10 |
| 4,988,362 | 1/1991 | Toriyama et al. | 523/115 |
| 5,063,257 | 11/1991 | Akahane et al. | 523/117 |

FOREIGN PATENT DOCUMENTS

| | | | |
|---|---|---|---|
| 0241277 | 4/1987 | European Pat. Off. | |
| 9112212 | 2/1990 | Fed. Rep. of Germany | |
| 2485504 | 6/1980 | France | |
| 1-076861 | 3/1989 | Japan | 523/113 |
| 1316129 | 5/1973 | United Kingdom | |

*Primary Examiner*—Paul R. Michl
*Assistant Examiner*—La Vonda DeWitt
*Attorney, Agent, or Firm*—Olson & Hierl, Ltd.

[57] ABSTRACT

Medical or dental hardening compositions of the present invention comprise calcium phosphate type devitrification glass-ceramics powder containing apatite and/or calcium phosphate ceramics and a liquid component. The second medical or dental hardening compositions of the present invention comprise strontium phosphate type devitrification glass-ceramics powder containing strontium-apatite crystals and/or calcium strontium phosphate ceramics, or calcium strontium phosphate type devitrification glass-ceramics powder and a liquid component.

11 Claims, 3 Drawing Sheets

MEDICAL OR DENTAL HARDENING COMPOSITIONS

FIELD OF THE INVENTION

This invention relates to medical or dental hardening compositions and, more particularly, to medical or dental hardening compositions, which are inorganic materials or composite materials made of inorganic materials and organic materials, and used as a bone cement or dental cement to fill or to fit prosthesis in defects or voids produced in bones or teeth by illness or external reasons. The medical or dental hardening compositions allow the treated part to form a new bone or tooth, and later become monolithic with the osseous tissue or dental tissue. This invention further pertains to hardening compositions for filling bones and teeth, which act as X-ray opacity material thus use allowing easy and accurate postoperative observation.

BACKGROUND OF THE INVENTION

Defects or voids are caused in bones or teeth by traffic accidents and ablation of osteoncus in the fields of surgery and orthopaedic surgery, and by periodontoclasia, alveoloclasia, odontectomy and cutting-off of dental caries in the field of dental surgery. Various materials including one's own bone, polymers, metals, ceramics etc. have been used to fill such defects and voids, as well as for the dental prosthesis. Among them, one's own bone is excellent since it has high bone forming capacity and causes little rejection. However, as one's own bone must be taken from the one's normal bone tissue, the operation causes great pain and in many cases not enough tissue can be secured. Thus, recently, hydroxyapatite has been replacing the use of one's own bone tissue. Hydroxyapatite can be obtained by synthesized or by sintered animal bones, and removing organic components, and it is known to have excellent biocompatibility. However, when hydroxyapatite in powder or granular form is used as a filling material, such problems as the tendency for it to run-off with blood or body fluids, or transuded as a foreign body even after suturing have been pointed out.

For cementing and fitting a prosthesis in the hard tissue bone-cement has been used. As the bone-cement, so called medical polymers based on PMMA (polymethyl methacrylate) have been used in most cases, however, these materials show insufficient biocompatibility and have such problems as the pain in the affected part caused by the reaction heat generated during the hardening reaction, or the harmfulness of the non-reached monomer to the living body.

Meanwhile, a dental cement material has been used not only as a coalescent for prosthesis, but also as a filling material or a lining material, and various dental cement materials have been developed as restortion materials in the field of dental surgery. Among them, glass ionomer cement, as shown in British Patent Number 1,316,129 made of glass powder produced by melting alumina and silica at a high temperature using a flux such as fluoride, and a hardening liquid made of a copolymer of acrylic acid and an unsaturated carboxylic acid, exhibits great crushing resistance after hardening, relatively good adhesion to tooth, and minimum harmfulness to dental pulp. However, it has a problem of insufficient biocompatibility.

In this context, a new dental cement made of such inorganic components that constitute the hard tissue have recently been drawing attention, and cements based on calcium phosphate or apatite type crystalline powder have been under development as well. The main components of these materials are bone analogues and have excellent biocompatibility, but the reactivity of the crystalline powder with an organic hardening liquid is very bad, since the components that react with the hardening liquid are very limited. Compositions for filling bones and teeth comprising $\alpha$-tricalcium phosphate and a liquid component, have been disclosed in U.S. Pat. No. 4,677,140, however, since the crushing resistance of the cement is very low, they cannot be employed for practical use.

Those dental cement materials developed so far have different merits and demerits respectively, and need to be chosen according to the particular purpose, however, the commonly required characteristics of a dental cement material include sufficient hardening characteristics and biocompatibility, and a material satisfying both of them has been desired.

In addition, no materials having both biocompatibility and X-ray opacity have been found for the medical or dental uses. It is needless to say that biocompatibility is very important for a biomaterial, but, in the case of an artificial material to be implanted in a body in some way, it is also important to know the condition of the artificial material when it is implanted, or to follow its change with time correctly. Thus, X-ray opacity also becomes an important property. In order to render X-ray opacity, a metal oxide or a metal salt of such a metal as strontium, barium or lanthanum have been typically blended as X-ray opacity material with the base material. However, those X-ray opacity components do not have biocompatibility, and have high solubility in a living body, or have problems in causing harmful effects including allergies. In view of the above-described problems, a material whose X-ray opacity component per se has biocompatibility and which can remain stable in a living body has also been strongly desired.

SUMMARY OF THE INVENTION

In order to solve the above-described technical problems, the present invention is aimed at, as is clear from the above description, providing medical or dental hardening compositions having sufficient hardening capacity and strength as well as excellent biocompatibility which are required for prosthesis and filling materials.

Another object of the present invention is to provide medical or dental hardening compositions having X-ray opacity as well.

GENERAL DESCRIPTION OF THE INVENTION

Figure 1:
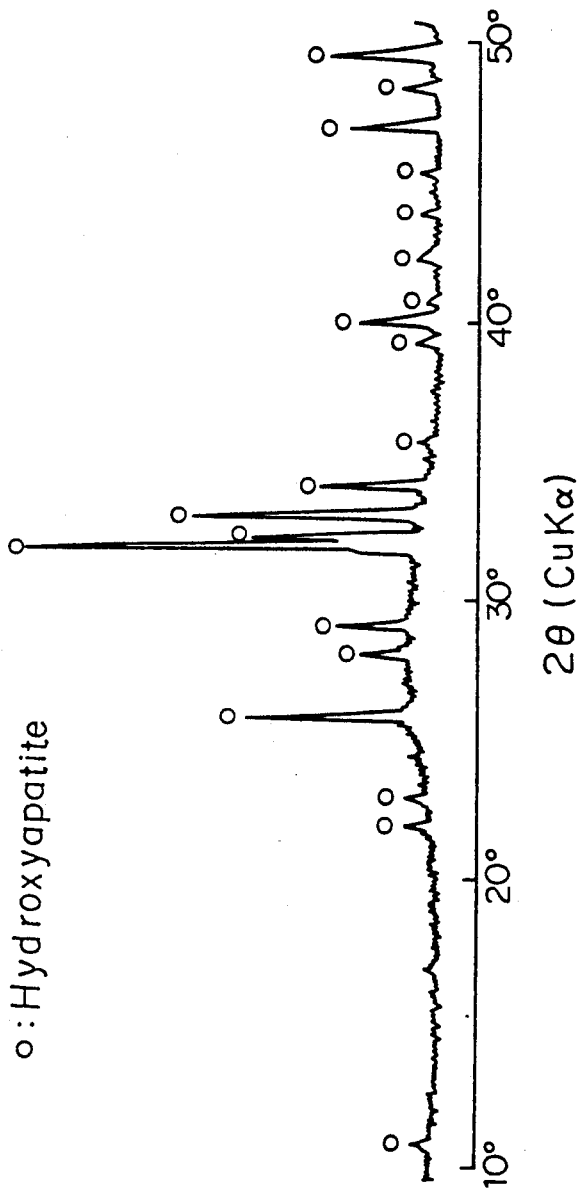
FIG. 1 is an X-ray diffraction pattern of calcium phosphate type devitrification glass-ceramics powder obtained in Example 2.

The medical or dental hardening compositions of the present invention which attained the above mentioned first object is basically made of calcium phosphate type devitrification glass-ceramics powder containing apatite and/or calcium phosphate ceramics and a liquid component.

After having carried out various experiments to develop medical or dental hardening compositions satisfying the above-described requirements, the present inventors have found that mixing calcium phosphate type devitrification glass-ceramics powder containing apatite ceramics and/or calcium phosphate crystal with various liquids provide hardening compositions showing both good hardening capacity and biocompatibility.

The medical or dental hardening compositions of the present invention which attained the above mentioned second object is basically made of strontium phosphate type devitrification glass-ceramics powder containing strontium-apatite and/or strontium phosphate ceramics, or calcium strontium phosphate type devitrification glass-ceramics powder containing strontium substituted apatite ceramics and a liquid component.

We have also found that mixing strontium phosphate type devitrification glass-ceramics powder containing strontium-apatite and/or strontium phosphate ceramics, or calcium strontium phosphate type devitrification glass-ceramics powder containing strontium substituted apatite ceramic with various liquids, provide hardening compositions having good hardening capacity, biocompatibility and X-ray opacity.

An exemplary explanation of the present invention will be given as follows.

The calcium phosphate type devitrification glass-ceramics powder of the present invention must contain apatite and/or calcium phosphate ceramics. These ceramics are the main components of bone, and accelerate the formation of a new bone. Calcium phosphate type devitrification glass-ceramics is not produced by simply adding and mixing these ceramics with glass: it must be devitrification glass with crystallized and stabilized ceramics dispersed therein. The ceramics phase is indispensable for attaining biocompatibility. The coexistence of glass in the ceramics is also an essential condition. This glass is indispensable as it provides excellent hardening capacity, and only so called devitrification glass-ceramics where the ceramics and glass are coexist, can provide hardening compositions showing both good biocompatibility and good hardening capacity. To generate these ceramics, appropriate amounts of calcium and phosphate salts, which become the main components, must be added to the raw materials. Particularly, since a feature of the present invention resides in the point that the devitrification glass-ceramics is produced by quickly cooling melted glass product and crystallizing a portion thereof without re-heating or gradually cooling melted glass to be crystallized, the selection and the blending of the raw materials for devitrification are very important. To produce so called crystallized glass in a normal process, either produced glass is re-heated or melted glass is gradually cooled, however, the calcium phosphate type devitrification glass-ceramics of the present invention is produced by quenching the glass in a molten condition to devitrify it, thus, highly active devitrification glass-ceramics can be obtained. The term "highly activity" means that reaction components can be easily provided to the various liquids to be described later so that hardening compositions of good physical properties can thus be obtained. These "physical properties" include hardening time, strength of the hardened mass and stability to dissolution.

An exemplary raw material chemical composition of calcium phosphate type devitrification glass-ceramics powder of the present invention is shown as follows:
CaO: 20–60% by weight
$P_2O_5$: 5–32% by weight
$SiO_2$: 15–30% by weight
$Al_2O_3$: 3–37% by weight
$F_2$: 1–10% by weight
MgO: 0–2% by weight The reasons for limiting the chemical composition of the calcium phosphate type devitrification glass-ceramics powder will be described as follows. If the content of CaO is below 20% by weight, the calcium phosphate type ceramics mainly containing hydroxyapatite will not form, resulting in poor biocompatibility, and conversely a content of over 60% will result in a decrease in the glass component in the total. Namely, means the component involving the hardening reaction is decreased, resulting in inferior hardening characteristics.

If the content of $P_2O_5$ is below 5% by weight, calcium phosphate type ceramics will not be formed, there will be no affinity to an organism, and if it is over 32% by weight, the resulting chemical resistance may be inferior with corrosion thereof in the organism occurring undesirably.

If the content of $SiO_2$ is below 15% by weight, the glass component rate in the total is decreased, and the clarity is lowered, and if it is over 30% by weight, the rate of the calcium phosphate ceramics in the glass-ceramics powder becomes relatively small, and low biocompatibility.

If the content of $Al_2O_3$ is below 3% by weight, glass strength is lowered, and if it is over 37% by weight, biocompatibility will decrease in the same manner as the case of $SiO_2$.

$F_2$ is effective as a flux, and if it is applied in the dental field, addition in the amount of 1–10% by weight will show a slow fluorine releasing effect, but if it is over 10% by weight, the original mechanical strength and the chemical resistance of the devitrification glass-ceramics itself may be lowered.

More than one component chosen from the group consisting of MgO, $Na_2O$ and $B_2O_3$ may be added to control the melting temperature of the glass or to control the amount of ceramics to be generated. However, if it is added in a large quantity, it may excessively control the crystallization of the calcium phosphate type ceramics, and result in lowering of biocompatibility. Accordingly, the amount of such component to be added is not more than 2% by weight.

The strontium phosphate type devitrification glass-ceramics powder or calcium strontium phosphate type devitrification glass-ceramics powder of the present invention must contain strontium-apatite and/or strontium phosphate ceramics or stontium substituted apatite. These ceramics are very analogous to the main components of bone, and accelerate osteoconduction. This is not produced simply by adding and mixing those ceramics with glass; but this must be so-called devitrification glass-ceramics where the crystallized and stabilized ceramics is dispersed in the glass. The ceramics is indispensable for rendering the biocompatibility and X-ray opacity. The coexistence of the glass in the ceramics is also an essential condition. This glass is indispensable for providing excellent hardening capacity, and so-called devitrification glass-ceramics in which the ceramic and the glass co-exist provide good hardening compositions showing good biocompatibility, X-ray opacity and hardening capacity. In order to generate these ceramics, the raw materials must contain appropriate amounts of strontium salt, or calcium salt and phosphate salt compound which become the main components. Particularly, since a feature of the present invention resides in the point that the devitrification glass-ceramics is produced by quickly cooling the melted glass product and crystallizing a portion thereof without re-heating or gradually cooling melted glass to be crystallized, the selection and the blending of the raw materials for the devitrification are very important. To produce so called crystallized glass in a normal process, either produced glass is re-heated or melted glass is gradually cooled, however, the devitrification glass-ceramics of the present invention is produced by quenching cooling the glass in a molten condition to devitrificate it, thus, highly active devitrification glass-ceramics can be obtained. The term "highly activity" means that reaction components can be easily provided to the various liquids to be described later, so that hardening compositions of good physical properties can thus be obtained. These "physical properties" include hardening time, strength of the hardened mass and stability to dissolution.

An exemplary raw material chemical composition of strontium phosphate type devitrification glass-ceramics or calcium strontium phosphate type devitrification glass-ceramics powder of the present invention is shown as follows:

SrO: 3–55% by weight
CaO: 0–40% by weight
$P_2O_5$: 5–32% by weight
$SiO_2$: 15–30% by weight
$Al_2O_3$: 3–37% by weight
$F_2$: 1–10% by weight
MgO: 0–2% by weight SrO is indispensable as a component to render X-ray opacity, however, in the present invention, so-called X-ray opacity component is not simply added and mixed in order to render the X-ray opacity. Those materials shown low bioactivity, and have problems such as high dissolution capacity in organisms and harmfulness to cause allergies. A feature of the present invention is that the strontium, which is effective as a component to render the X-ray opacity, is not contained in the form of strontium oxide (SrO) but forms, in the generated devitrified glass, strontium apatite $[Sr_{10}(PO_4)_6(OH)_2]$, strontium phosphate or strontium substituted apatite $[Sr_xCa_{10-x}(PO_4)_6(OH)_2]$ having a structure analogous to the main components of bone or tooth.

The reasons for limiting the raw material composition of the strontium phosphate type devitrification glass-ceramics powder or calcium strontium phosphate type devitrification glass-ceramics powder are described as follows. If the content of SrO is below 3% by weight, it is not sufficient to render X-ray opacity, and if it is over 55% by weight, the glass component rate in the total is decreased, thus the component involving the hardening reaction is decreased, and the resulting hardening characteristics may be inferior. The appropriate content of CaO is between 0 and 40% by weight, and when it is 0% by weight, pure strontium-apatite or strontium phosphate ceramics is generated in the devitrified glass. When CaO is blended, strontium substituted apatite is generated. This is a solid solution and a apatite type ceramics that continuously changes structure depending on the ratio of the amounts of SrO and CaO will be generated. The blending ratio thereof can be changed freely depending on the desired crystal phase, or the desired X-ray opacity, but their total is preferably not more than 60% by weight. That is because, if the amount exceeds 60% by weight, the glass component rate in the total is decreased, thus the component involving the hardening reaction is decreased resulting in inferior hardening characteristics. Though the generated ceramics vary depending on the CaO content, all of them have a structure that is very analogous to the hard tissue, and show very high biocompatibility.

If the content of $P_2O_5$ is below 5% by weight, strontium phosphate ceramics or calcium strontium phosphate ceramics will not be formed, there will be no affinity to an organism, and if it is over 32% by weight, the resulting chemical resistance may be inferior, with corrosion thereof in the organism occurring undesirably.

If the content of $SiO_2$ is below 15% by weight, the glass component rate in the total is decreased to lower the clarity, and if it is over 30% by weight, the rate of the strontium phosphate ceramics or calcium strontium phosphate ceramics in the glass powder becomes relatively small, and biocompatibility is be lowered.

As for $Al_2O_3$, $F_2$, MgO, $Na_2O$, and $B_2O_3$, the above-mentioned description given for the calcium phosphate type devitrification glass-ceramics can be applied in the same way.

As a liquid component, one solution chosen from the group consisting of physiological saline solution, a water soluble polymer solution, an inorganic acid aqueous solution, an organic acid aqueous solution, an aqueous solution of a polymer of an unsaturated carboxylic acid and a mixture of these, is preferably employed. For example, for use as a dental cement, since strength must be displayed in a short time, an aqueous solution of a polymer of an unsaturated carboxylic acid having a concentration of 20–80% is preferably used. More preferably, an aqueous solution having a concentration of 40–60% to which an inorganic acid or an organic acid having the concentration of 20% or less is added to control the hardening characteristics, is employed.

For the use as a filling material for a defect in bones or a root canal, a physiological saline solution is recommended since it is free from the stimulus of an acid or an alkali, however, it is effective to add a suitable amount of a water soluble polymer such as CMC (sodium carboxymethyl cellulose) or polyethylene glycol, etc. to physiogical saline solution in order to render fluidity and viscosity.

The devitrification glass-ceramics of the present invention may contain small amounts of alkaline earth metal silicate ceramics such as wollastonite ($CaO.SiO_2$), diopside ($MgO.CaO.2SiO_2$), and forsterite ($2MgO.SiO_2$) in addition to hydroxyapatite, calcium phosphate ceramics, strontium-apatite, strontium phosphate ceramics, and strontium substituted apatite.

A hardening cementitous composition of this invention is thus initially prepared as a powder by the steps of melting a starting composition as above characterized, quenching the so melted composition preferably in water, and then grinding the so quenched composition into a powder. Grinding can be accomplished by any conventional procedure using conventional apparatus, such as a pot mill, jet mill, stamp mill, roll mill or the like. The resulting powder has an average particle size that is below about 100 micrometers and preferably is in the range of about 2 to about 10 micrometers.

Before use, the powder composition is dispersed in a liquid medium which is preferably aqueous. The weight ratio of a powder composition to the liquid medium can range widely, but a present preference is to employ a weight ratio that is in the range of about 1:0.1 to about 1:5.

EXAMPLES

Some examples of this invention will be described in further details as follows. It is to be understood that the following examples are simply illustrative of the invention, and other arrangements may be devised by those skilled in the art which will embody the principles of the invention and fall within the spirit and scope thereof.

EXAMPLE 1

Glass raw materials were prepared to have a composition of CaO: 43.1% by weight, $P_2O_5$: 18.6% by weight, $SiO_2$: 20.9% by weight, $Al_2O_3$: 11.9% by weight, MgO: 0.5% by weight, and $F_2$: 5.0% by weight. This was melted for 2 hours at 1600° C., then quenched in water to produce devitrification glass. Under X-ray diffractometry hydroxyapatite, tricalcium phosphate ceramics and glass were recognized.

The obtained devitrification glass-ceramics powder was then finely into a powder having an average particle size of 10 μm, a liquid component made of physiological saline solution and 1% CMC was added thereto at a ratio of 2 (powder) to 1 (liquid) by weight, and the setting time was found to be 6 hours.

This was next filled in medullary cavities drilled in two spots of a thigh bone of a three-week old Wistar rat, then cut out after three months, prepared into a polished thin section in a conventional manner, and observed by microscope. Newly formed bones was found to surround and penetrate the glass-ceramics powder, and the bonds were firm.

In place of the calcium phosphate type devitrification glass-ceramics having an average particle size of 10 μm, a mixture of aluminosilicate glass powder having an average particle size of 10 μm and hydroxyapatite crystal powder having an average particle size of 10 μm (a mixing ratio of 1:1 by weight) was filled in medullary cavities drilled at two spots of a thigh bone of a three-week old Wistar rat in the same way as in Example 1, and cut out after three months, prepared into a polished thin section in a conventional manner, then observed by microscope to find one layer of newly formed bone around the filled part.

EXAMPLE 2

Glass raw materials were prepared to have the composition of CaO: 32.0% by weight, $P_2O_3$: 9.0% by weight, $SiO_2$: 24.5% by weight, $Al_2O_3$: 29.0% by weight, MgO: 0.5% by weight, and $F_2$: 5.0% by weight. This was melted for 2 hours at 1600° C., then quenched in air to produce devitrification glass. This was finely ground into a powder having an average particle size of 3 μm by a pot mill. X-ray diffractometry showed that a glass and ceramics co-existed, that the ceramics was hydroxyapatite, and that the ratio of the glass to the hydroxyapatite was 7:3. The results are shown in the FIG. 1.

A liquid component made of 40% by weight of polycarboxylic acid having an average molecular weight of about 15000, which was produced from itaconic acid (40% by weight) and acrylic acid (60% by weight), 10% by weight of tartaric acid, and 50% by weight of water was added to the obtained devitrification glass-ceramics powder at the weight ratio of 1.2 (powder) to 1 (liquid), and the resulting product was then tested in accordance with "JIS T-6602". The obtained cement showed a hardening time of 4 minutes, a compression strength after 24 hours of 1460 kg/cm$^2$, and a dissolution rate in 24 hours of 0.09%. When the liquid was mixed with the powder at the weight ratio of 1.8 (powder) to 1 (liquid), the resulting cement showed a hardening time of 4 minutes 30 seconds, and a compression strength after 24 hours of 1810 kg/cm$^2$.

EXAMPLE 3

Glass raw materials were prepared to have the compositions shown in the following Table I, and melted at 1400°–1650° C., then quenched in water to produce devitrification glass-ceramics (Samples No. 1–7). They were pulverized by a pot mill to have an average particle size of 2–5 μm. 1.0 part by weight of a liquid component made of 40% by weight of polyacrylic acid, 10% by weight of tartaric acid and 50% by weight water was added to 1.6 parts by weight of the devitrification glass-components powder, then ground, and the properties of the obtained hardened mass were investigated. The list contains the results identification of the crystal phase identification by X-ray diffractometry, hardening time, and the compression strength after 24 hours. Products obtained by formulating the glass raw materials of samples No. 8–11 followed by known nucleated glass production process, and hydroxyapatite powder (Sample No. 12) were examined on the same points as the comparative examples. As especially remarkable point was that the products of the present invention showed a compression strength of 1150–1600 kg/cm$^2$, while the comparative examples, samples No. 8–12 showed low values between 50–400 kg/cm$^2$.

TABLE I

| Sample No. | Chemical composition (% by weight) | | | | | | Crystal phase (1) | Hardening time (2) | Compression strength (kg/cm$^2$) |
| --- | --- | --- | --- | --- | --- | --- | --- | --- | --- |
| | CaO | $P_2O_5$ | $SiO_2$ | $Al_2O_3$ | MgO | $F_2$ | | | |
| 1 | 49.8 | 24.6 | 16.3 | 3.8 | 0.5 | 5.0 | H | 2 min | 1150 |
| 2 | 45.4 | 20.7 | 20.1 | 8.3 | 0.5 | 5.0 | H | 2.5 min | 1210 |
| 3 | 40.8 | 16.5 | 21.8 | 15.4 | 0.5 | 5.0 | H | 3.5 min | 1280 |
| 4 | 36.2 | 12.2 | 23.4 | 22.7 | 0.5 | 5.0 | H | 4 min | 1360 |
| 5 | 32.0 | 9.0 | 24.5 | 29.0 | 0.5 | 5.0 | H | 4 min | 1460 |
| 6 | 31.6 | 7.9 | 25.0 | 30.0 | 0.5 | 5.0 | H | 4.5 min | 1600 |
| 7 | 28.0 | 7.0 | 25.0 | 30.0 | 0.5 | 9.5 | H | 4 min | 1320 |
| 8 | 15.0 | 2.5 | 71.8 | 10.0 | 0.5 | 0.2 | G | 10 sec | 57 |
| 9 | 27.0 | 5.0 | 31.0 | 30.0 | 2.0 | 5.0 | A/H | 10 min | 50 |
| 10 | 20.0 | 5.0 | 38.0 | 30.0 | 2.0 | 5.0 | A | 15 min | 63 |
| 11 | 14.9 | 6.9 | 35.0 | 30.4 | 1.7 | 11.1 | A/H | 1 hr | 115 |

TABLE I-continued

| Sample No. | Chemical composition (% by weight) | | | | | | Crystal phase (1) | Hardening time (2) | Compression strength (kg/cm²) |
|---|---|---|---|---|---|---|---|---|---|
| | CaO | P₂O₅ | SiO₂ | Al₂O₃ | MgO | F₂ | | | |
| 12 | Hydroxyapatite powder | | | | | | H | 9 min | 370 |

(1) H: Hydroxyapatite, A: Anorthite, G: Glass
(2) The ratio of powder to liquid = 1.2:1
(3) Samples No. 1-7: products of the present invention, and Samples No. 8-12: comparative examples.

EXAMPLE 4

Figure 2:
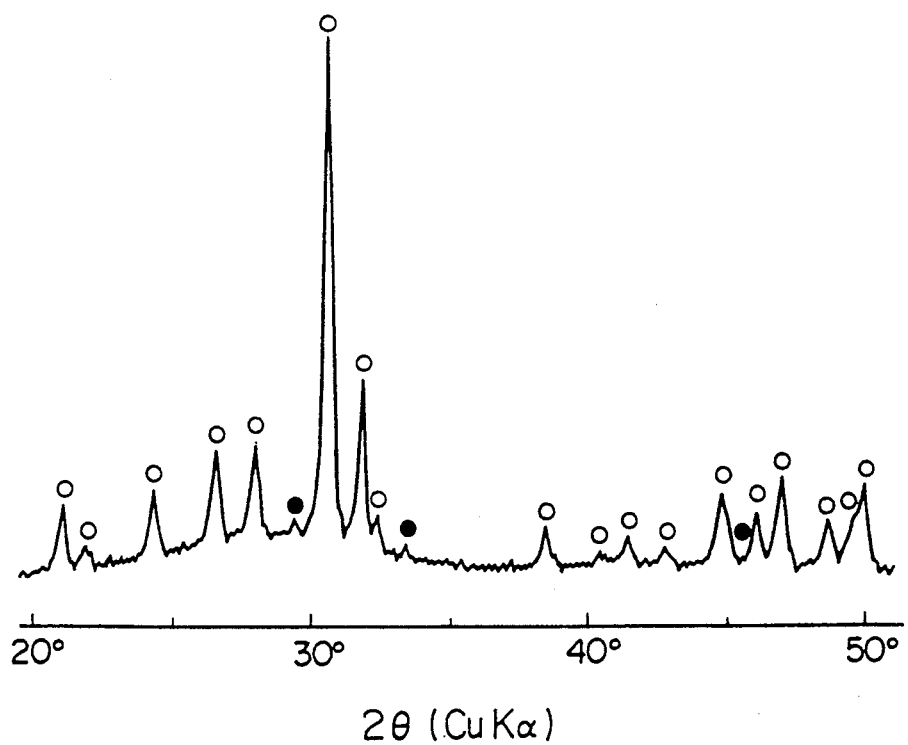
FIG. 2 is an X-ray diffraction pattern of strontium phosphate type devitrification glass-ceramics powder obtained in Example 4.

Glass raw materials were prepared to have a composition of SrO: 36.2% by weight, $P_2O_5$: 12.2% by weight, $SiO_2$: 23.4% by weight, $Al_2O_3$: 22.7% by weight, MgO: 0.5% by weight, and $F_2$: 5.0% by weight. This was melted for 2 hours at 1600° C., then quenched in water to produce devitrification glass-ceramics. Under X-ray diffractometry strontium-apatite, tristrontium phosphate and glass were recognized. The results are shown in the FIG. 2.

The obtained devitrification glass-ceramics powder was then finely ground int a powder having an average particle size of 10 μm, a liquid component made of physiological saline solution and 1% CMC was added thereto it at a ratio 2 (powder) to 1 (liquid) by weight, and the setting time was found to be 8 hours. The X-ray opacity was equivalent to that of a pure aluminum plate of 6 mm.

This was next filled in medullary cavities drilled it two spots of a thigh bone of a mongrel adult dog and X-ray radiographic inspection was carried out. The filling substance showed up clearly taken. After 3 months, this was cut out and prepared into a polished thin section in a conventional manner, then observed by microscope to find that newly formed bone surrounded and penetrated the glass-ceramics powder, and that the bonds were firm.

In place of the strontium phosphate type devitrification glass-ceramics having an average particle size of 10 μm, a mixture of aluminosilicate glass powder having an average particle size of 10 μm and hydroxyapatite powder having an average particle size of 10 μm (a mixing ratio of 1:1 by weight) was filled in medullary cavities drilled at two spots of a thigh bone of a mongrel adult dog in the same way as in Example 4, and checked by X-ray, but no clear difference between the surrounding part and the filling material was recognized. It was cut out after three months, prepared into a polished thin section in a conventional manner, then observed by microscope to find one layer of new bone around the filling material.

EXAMPLE 5

Figure 3:
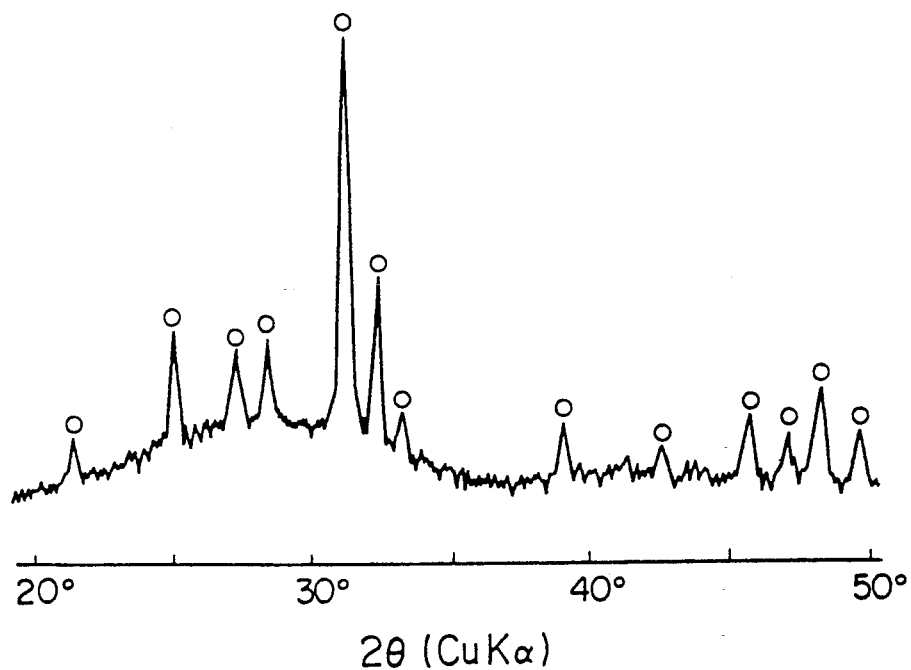
FIG. 3 is an X-ray diffraction pattern of calcium strontium phosphate type devitrification glass-ceramics powder obtained in Example 5.

Glass raw materials were prepared to have the composition of SrO: 27.8% by weight, CaO: 12.0% by weight, $P_2O_3$: 7.0% by weight, $SiO_2$: 22.0% by weight, $Al_2O_3$: 26.4% by weight, MgO: 0.5% by weight, and $F_2$: 4.4% by weight. This was melted for 2 hours at 1600° C., then quenched in air to produce devitrification glass-ceramics. It was finely ground into a powder having an average particle size of 3 μm by a pot mill. X-ray diffractometry carried out on the obtained devitrification glass-ceramics powder showed coexisting glass and ceramics, that the ceramics was strontium substituted apatite, and that the ratio of the glass to the ceramics was 7:3. The results are shown in FIG. 3.

A liquid component made of 40% by weight of polycarboxylic acid having an average molecular weight of about 15000, which was produced from itaconic acid (40% by weight) and acrylic acid (60% by weight), 10% by weight of tartaric acid, and 50% by weight of water was added to the obtained devitrification glass-ceramics powder at the weight ratio of 1.2 (powder) to 1 (liquid), the resulting product was then tested in accordance with "JIS T-6602". The obtained cement showed a hardening time of 6 minutes, a compression strength after 24 hours of 1240 kg/cm², and a dissolution rate in 24 hours of 0.28%. When the liquid was mixed with the powder at the weight ratio of 1.8 (powder) to 1 (liquid), the resulting cement showed a hardening time of 5 minutes and a compression strength after 24 hours of 1630 kg/cm². The X-ray opacity of the product was equivalent to that of a pure aluminum plate of 5 mm.

EXAMPLE 6

Glass raw materials were prepared to have the compositions shown in the following Table II, and melted at 1400°-1650° C., then quenched in water to produce devitrification glass-ceramics (Samples No. 1-3). They were pulverized by a pot mill to have an average particle size of 2-5 μm. 1.0 part by weight of a liquid component made of 40% by weight of polyacrylic acid, 10% by weight of tartaric acid and 50% by weight of water was added to 1.6 parts by weight of the devitrification glass-ceramics powder, then ground, and the properties of the obtained cements were investigated. The list contains the results of the crystal phase identification by X-ray diffractometry, hardening time, the compression strength after 24 hours, and X-ray opacity. Products obtained by formulating the glass raw materials of samples No. 4-6 followed by known nucleated glass production process, and hydroxyapatite crystal powder (sample No. 8) were examined on the same points as comparative examples. An especially remarkable point was that the products of the present invention showed a compression strength of 1040-1680 kg/cm², while the comparative examples, samples No. 4-8 showed low values between 50-400 kg/cm².

TABLE II

| Sample No. | Chemical composition (% by weight) | | | | | | | Crystal phase (1) | Hardening time (2) | Compression strength (kg/cm²) | X-ray opacity (3) |
|---|---|---|---|---|---|---|---|---|---|---|---|
| | SrO | CaO | P₂O₅ | SiO₂ | Al₂O₃ | MgO | F₂ | | | | |
| 1 | 25.0 | 6.6 | 7.9 | 25.0 | 30.0 | 0.5 | 5.0 | S | 7 min | 1040 | 5 |
| 2 | 11.7 | 19.9 | 7.9 | 25.0 | 30.0 | 0.5 | 5.0 | S | 5 min | 1390 | 3 |
| 3 | 5.0 | 26.6 | 7.9 | 25.0 | 30.0 | 0.5 | 5.0 | S | 3 min | 1680 | 2 |
| 4 | 0 | 15.0 | 2.5 | 71.8 | 10.0 | 0.5 | 0.2 | G | 10 sec | 57 | 1 |
| 5 | 0 | 27.0 | 5.0 | 31.0 | 30.0 | 2.0 | 5.0 | H/A | 10 min | 50 | 2 |

TABLE II-continued

| Sample No. | Chemical composition (% by weight) | | | | | | | Crystal phase (1) | Hardening time (2) | Compression strength (kg/cm²) | X-ray opacity (3) |
|---|---|---|---|---|---|---|---|---|---|---|---|
| | SrO | CaO | $P_2O_5$ | $SiO_2$ | $Al_2O_3$ | MgO | $F_2$ | | | | |
| 6 | 0 | 20.0 | 5.0 | 38.0 | 30.0 | 2.0 | 5.0 | A | 15 min | 63 | 1 |
| 7 | 0 | 14.9 | 6.9 | 35.0 | 30.4 | 1.7 | 11.0 | H/A | 1 hr | 115 | 1 |
| 8 | 0 | Hydroxyapatite powder | | | | | | H | 9 min | 370 | 1 |

(1) S: Strontium substituted apatite, H: Hydroxyapatite, A: Anorthite, G: Glass
(2) The ratio of powder to liquid = 1.6:1
(3) X-ray opacity was evaluated by X-ray radiographic inspection using a dental roentgen device and pure aluminium plates having 10 different thicknesses varying from 1 mm to 10 mm and a sample having a thickness of 1 mm. The X-ray opacity of the sample is shown in terms of the thickness of the aluminum plate having equivalent transmissivity. Conditions and Device: SUNEXRAY D-65-S, Tube Voltage: 65Kvp, Tube current: 10 mA, Distance: 300 mm, Irradiation time: 0.7 sec, Film: Kodak NF-55
(4) Samples No. 1-3: products of the present invention, Samples No. 4-8: comparative examples.

As it is also clear from the above-described results, it can be understood that the medical or dental hardening compositions satisfying the requirements specified in the present invention show good hardening characteristics and good biocompatibility.

As it is clear from the above description, new medical or dental hardening compositions showing good hardening capacity, sufficient compression strength and good biocompatibility can be provided in accordance with the present invention. By the use of strontium phosphate type devitrification glass-ceramics powder containing strontium-apatite or strontium phosphate apatite or calcium strontium phosphate type devitrification glass-ceramics powder containing strontium substituted apatite, the resulting medical or dental hardening compositions show good X-ray opacity as well.

We claim:

1. A hardening cementitious composition for prosthetic and filling usage in dental and medical applications comprising a devitrified glass-ceramic powder wherein a ceramic phase is present in a glass matrix phase which powder is dispersed in an aqueous liquid,
   said ceramic phase being comprised of a material selected from the group consisting of calcium phosphate apatite, strontium substituted apatite, strontium phosphate and mixtures thereof,
   said powder having been prepared by the steps of:
   (a) melting at a temperature in the range of about 1400° to about 1650° C. a starting mixture comprising on a 100 weight percent basis:
   0–60 weight percent CaO
   3–55 weight percent SrO
   5–32 weight percent $P_2O_5$
   15–30 weight percent $SiO_2$
   3–37 weight percent $Al_2O_3$
   1–10 weight percent $F_2$
   0–2 weight percent of a material selected from the group consisting of $M_gO$, $Na_2O$, $B_2O_3$ and mixtures thereof, provided that:
   when CaO is present without SrO, the amount of CaO present is at least about 20 weight percent, and
   when CaO and SrO are both present their total amount is not more than about 60 weight percent, and also the amount of CaO is not more than about 40 weight percent;
   (b) quench cooling the resulting melt to a solid; and
   (c) grinding said solid into a powder having an average particle size that is below about 100 micrometers.

2. The composition of claim 1 wherein the weight ratio of said powder to said aqueous liquid is in the range of about 1:0.1 to about 1:5.

3. The composition of claim 1 wherein said ceramic phase is comprised of a material selected from the group consisting of calcium phosphate, apatite, and mixtures thereof, and said starting mixture comprises on a 100 weight percent basis:
   20–60 weight percent CaO
   5–32 weight percent $P_2O_5$
   15–30 weight percent $SiO_2$
   3–37 weight percent $Al_2O_3$
   1–10 weight percent $F_2$
   0–2 weight percent of a material selected from the group consisting of $M_gO$, $Na_2O$, $B_2O_3$ and mixtures thereof.

4. The composition of claim 1 wherein said starting mixture comprises on a 100 weight percent basis:
   3–55 weight percent SrO
   0–40 weight percent CaO
   5–32 weight percent $P_2O_5$
   15–30 weight percent $SiO_2$
   3–37 weight percent $Al_2O_3$
   1–10 weight percent $F_2$
   0–2 weight percent of material selected from the group consisting of $M_gO$, $Na_2O$, $B_2O_3$ and mixtures thereof.

5. The composition of claim 1 wherein said aqueous liquid contains dissolved therein a member of the group consisting of sodium chloride, water soluble polymer, inorganic acid, organic acid and mixtures thereof.

6. The composition of claim 5 wherein said water soluble polymer is comprised of an unsaturated carboxylic acid.

7. A method for preparing a hardening cementitious composition for prosthetic and filling usage in dental and medical applications comprising the steps of:
   (a) melting at a temperature in the range of about 1400° to about 1650° C. a starting mixture comprising on a 100 weight percent basis:
   0–60 weight percent CaO
   3–55 weight percent SrO
   5–32 weight percent $P_2O_5$
   15–30 weight percent $SiO_2$
   3–37 weight percent $Al_2O_3$
   1–10 weight percent $F_2$
   0–2 weight percent of a material selected from the group consisting of $M_gO$, $Na_2O$, $B_2O_3$ and mixtures thereof, provided that:
   when CaO is present without SrO, the amount of CaO present is at least about 20 weight percent, and
   when CaO and SrO are both present their total amount is not more than about 60 weight percent and the amount of CaO is not more than about 40 weight percent;
(b) quench cooling the resulting melt to a solid;
(c) grinding said solid into a powder having an average particle size that is below about 100 micrometers; and
(d) dispersing said powder in an aqueous liquid so that the weight ratio of said powder to said liquid is in the range of about 1:0.1 to about 1:5.

8. The method of claim 7 which includes the step of dissolving in said liquid a member of the group consisting of sodium chloride, water soluble polymer, inorganic acid, organic acid, and mixtures thereof.

9. The method of claim 8 wherein said water soluble polymer is comprised of an unsaturated carboxylic acid.

10. The method of claim 7 wherein said starting mixture comprises on a 100 weight percent basis:
20-60 weight percent CaO
5-32 weight percent $P_2O_5$
15-30 weight percent $SiO_2$
3-37 weight percent $Al_2O_3$
1-10 weight percent $F_2$ and
0-2 weight percent of a material selected from the group consisting of $M_gO$, $Na_2O$, $B_2O_3$ and mixtures thereof.

11. The composition of claim 7 wherein said starting mixture comprises on a 100 weight percent basis:
3-55 weight percent SrO
0-40 weight percent CaO
5-32 weight percent $P_2O_5$
15-30 weight percent $SiO_2$
3-37 percent $Al_2O_3$
1-10 weight percent $F_2$ and
0-2 weight percent of material selected from the group consisting of $M_gO$, $Na_2O$, $B_2O_3$ and mixtures thereof.

* * * * *